(12) United States Patent
Park et al.

(10) Patent No.: US 8,673,944 B2
(45) Date of Patent: Mar. 18, 2014

(54) SOLID PHARMACEUTICAL COMPOSITION COMPRISING AMLODIPINE AND LOSARTAN WITH IMPROVED STABILITY

(75) Inventors: Jae Hyun Park, Suwon-si (KR); Kyeong Soo Kim, Suwon-si (KR); Ho Taek Yim, Yongin-si (KR); Ji Hyun Im, Suwon-si (KR)

(73) Assignee: Hanmi Science Co., Ltd, Hwaseong-si (KR)

( * ) Notice: Subject to any disclaimer, the term of this patent is extended or adjusted under 35 U.S.C. 154(b) by 291 days.

(21) Appl. No.: 13/139,426

(22) PCT Filed: Jun. 5, 2009

(86) PCT No.: PCT/KR2009/003028
§ 371 (c)(1),
(2), (4) Date: Jun. 13, 2011

(87) PCT Pub. No.: WO2010/085027
PCT Pub. Date: Jul. 29, 2010

(65) Prior Publication Data
US 2011/0245301 A1 Oct. 6, 2011

(30) Foreign Application Priority Data
Jan. 23, 2009 (KR) .......................... 10-2009-0005840
Apr. 24, 2009 (KR) .......................... 10-2009-0036011

(51) Int. Cl.
*A61K 31/44* (2006.01)
*A61K 31/41* (2006.01)
*A61K 9/20* (2006.01)

(52) U.S. Cl.
USPC ........................... 514/356; 514/381; 424/465

(58) Field of Classification Search
None
See application file for complete search history.

(56) References Cited

U.S. PATENT DOCUMENTS

| 6,677,356 B1 | 1/2004 | Sethi et al. |
| 2002/0068740 A1 | 6/2002 | Mylari |
| 2002/0099046 A1 | 7/2002 | Scott |

FOREIGN PATENT DOCUMENTS

| JP | 2008-543729 A | 12/2008 |
| WO | 03/035046 A2 | 5/2003 |
| WO | 03/097045 A1 | 11/2003 |
| WO | 2005/070463 A2 | 8/2005 |
| WO | 2007/056324 A2 | 5/2007 |
| WO | 2007/075009 A1 | 7/2007 |
| WO | 2008/044862 A1 | 4/2008 |
| WO | 2008/069612 A1 | 6/2008 |

OTHER PUBLICATIONS

Taiwanese Patent Office, Taiwanese Office Action issued in corresponding TW Application No. 098120461, dated Jul. 30, 2012.
New Zealand Patent Office, New Zealand Examination Report issued in corresponding NZ Application No. 594740, dated May 23, 2012.
Ukranian Patent Office, Ukrainian Office Action issued in corresponding Ukrainian Application No. 201110284, dated Feb. 12, 2013, with English-language translation.
Shayne Cox Gad, "Pharmaceutical Manufacturing Handbook: Production and Processes," John Wiley & Sons, Inc., 2008, pp. 1-1370.

*Primary Examiner* — Sreeni Padmanabhan
*Assistant Examiner* — Jody Karol
(74) *Attorney, Agent, or Firm* — Sughrue Mion, PLLC

(57) ABSTRACT

The present invention relates to a solid pharmaceutical composition for preventing or treating cardiovascular disorders comprising granular forms of amlodipine and losartan which are separated from each other, and a stabilizing agent, which has improved storage stability due to minimized interaction between amlodipine and losartan.

9 Claims, No Drawings

SOLID PHARMACEUTICAL COMPOSITION COMPRISING AMLODIPINE AND LOSARTAN WITH IMPROVED STABILITY

CROSS REFERENCE TO RELATED APPLICATIONS

This application is a National Stage of International Application No. PCT/KR2009/003028 filed Jun. 5, 2009, claiming priority based on Korean Patent Application No. 10-2009-0005840 filed Jan. 23, 2009 and Korean Patent Application No. 10-2009-0036011 filed Apr. 24, 2009, the contents of all of which are incorporated herein by reference in their entirety.

FIELD OF THE INVENTION

The present invention relates to a solid pharmaceutical composition for preventing or treating cardiovascular disorders comprising amlodipine and losartan, which has improved storage stability.

BACKGROUND OF THE INVENTION

In the treatment of hypertension to reduce the risks of complications such as coronary heart diseases and cardiovascular diseases, e.g., stroke, heart failure and myocardial infarction, it is more important to maintain the blood pressure within a normal range on a consistent basis than to simply lower the blood pressure level itself. Accordingly, antihypertensive agents are required to be effective for long-term treatment of hypertension. Further, advanced therapy using a combination of two or more drugs having different pharmacological actions makes it possible to improve preventive or therapeutic effects, while lowering side effects arising from the long term administration of a single drug.

Notable antihypertensive drugs include diuretics, sympatholytic agents and vasodilators. Vasodilators are most widely prescribed antihypertensive drugs, and they are divided into several groups according to their pharmacological actions which include ACE (angiotensin converting enzyme) inhibitors, angiotensin II receptor antagonists, and calcium channel blockers.

Amlodipine is the generic name for 3-ethyl-5-methyl-2-(2-aminoethoxy-methyl)-4-(2-chlorophenyl)-6-methyl-1,4-dihydro-3,5-pyridine dicarboxylate. Amlodipine besylate is currently marketed as Novasc (trade mark). Amlodipine is a long-acting calcium channel blocker which is useful in treating cardiovascular disorders such as angina, hypertension and congestive heart failure.

Losartan is the generic name for 2-butyl-4-chloro-1-[[2'-(1H-tetrazol-5-yl)[1,1'-biphenyl]-4-yl]methyl]-1H-imidazol-5-methanol, which has been disclosed in U.S. Pat. Nos. 5,608,075; 5,138,069; and 5,153,197. Losartan potassium is commercially available as Cozaar (trade mark). Losartan blocks the interaction of angiotensin II and its receptor, and is mainly used for treating hypertension, heart failure, ischemic peripheral circulatory disorder, myocardial ischemia (angina pectoris), diabetic neuropathy and glaucoma, and also for preventing the progression of post-myocardial infarction heart failure.

The present inventors have found that a combined formulation which comprises amlodipine and losartan having different pharmacological activities is useful for preventing or treating cardiovascular disorders, and have conducted intensive studies on such a combined formulation. However, the development of a stable amlodipine-losartan combined formulation which can be reproducibly and easily prepared has been hard to achieve mainly because of difficulties in handling the two drugs.

Amlodipine is generally used in the formulation in the form of an acid-addition salt with a pharmaceutically acceptable acid which is more stable and exhibits a higher water-solubility than a free base form of amlodipine.

It is reported that amlodipine malate, one of such acid-addition salts of amlodipine, tends to gradually decompose with time after formulation into amlodipine aspartate of formula (I) or amlo-pyridine of formula (II), to lower the efficacy of a pharmaceutical composition comprising same (U.S. Pat. No. 6,919,087). Amlodipine besylate which is commercially available and disclosed in EP 244944 (corresponding U.S. Pat. No. 4,879,303) has been recently placed in general use, but it also suffers the above-mentioned problems such as decomposition and poor storage stability.

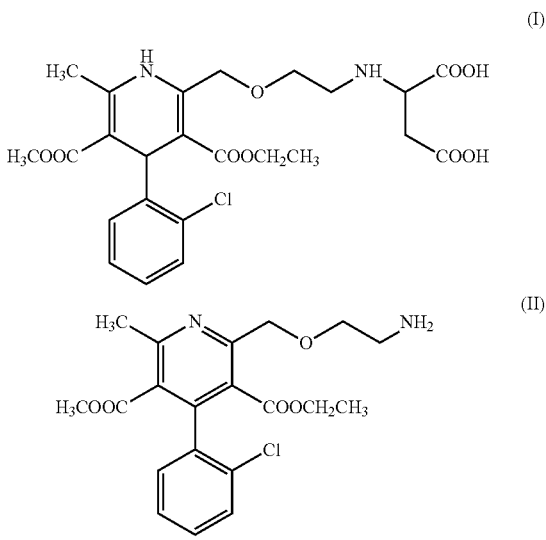

The present inventors have developed camsylate salt of amlodipine which exhibits improved properties in terms of solubility and stability than amlodipine besylate, and the camsylate salt is currently marketed as Amodipine (trade mark). It has been found, however, that when formulated by simple mixing with losartan, amlodipine camsylate exhibits very poor storage stability presumably due to undesired chemical interactions among amlodipine, losartan and excipients.

It is well known that when heated under an acidic condition, losartan potassium also decomposes to form products referred to as degradate E or F (see [Z. Zhao et al., *J. Pharm. Biomed. Anal*, 20: 129-136, 1999]). Further, in case that losartan is formulated in the form of a combined formulation by simple mixing with an acid-addition salt of amlodipine, the acidic component of the amlodipine salt destabilizes losartan.

SUMMARY OF THE INVENTION

Accordingly, it is an object of the present invention to provide a solid pharmaceutical composition containing amlodipine and losartan, which has improved storage stability due to minimized interaction between the two drugs, amlodipine and losartan.

In accordance with one aspect of the present invention, there is provided a solid pharmaceutical composition for preventing or treating cardiovascular disorders comprising granular forms of amlodipine and losartan which are separated from each other, and a stabilizing agent.

Preferably, the stabilizing agent may be an anti-oxidant.

DETAILED DESCRIPTION OF THE INVENTION

The solid pharmaceutical composition of the present invention comprising separated granule forms of amlodipine and losartan as well as a stabilizing agent has the feature of minimized interaction between the two drugs, which leads to markedly improved storage stability.

Amlodipine used in the present invention may be one of various forms of pharmaceutically acceptable salts. The pharmaceutically acceptable salts of amlodipine include hydrochloride, hydrobromide, sulphate, phosphate, acetate, maleate, fumarate, lactate, tartrate, citrate, gluconate, besylate and camsylate salts, but are not limited thereto. Among these salts, preferred are the amlodipine besylate and camsylate, and more preferred is the amlodipine camsylate. Also, amlodipine used in the present invention may be racemic amlodipine or S-amlodipine.

Losartan used in the present invention may be one of various forms of pharmaceutically acceptable salts. The preferred pharmaceutically acceptable salt of losartan is losartan potassium.

In the inventive composition, amlodipine and losartan may be used in amounts corresponding to a weight ratio in the range of 1:1 to 1:40, preferably 1:2 to 1:20.

When the combined formulation of amlodipine and losartan is prepared by simply mixing the two drugs, undesirable gelation of losartan occurs, and amlodipine may be entrapped within the gel, making the release of amlodipine difficult.

In order to overcome such a losartan gelation problem, a method that employ a separating layer between amlodipine and losartan is disclosed in Korean Patent Application Publication No. 2008-0052852. However, the separating layer formed by this method does not significantly improve the storage stability for the reason that relatively rapid decomposition of amlodipine occurs due to incomplete prevention of the chemical interaction between amlodipine or an acid-addition salt thereof and losartan. As a matter of fact, the combined formulations of Comparative Examples 3 and 4, which were prepared by physically separating amlodipine from losartan and separately granulating them, generate impurities related to amlodipine decomposition in amounts that are more than 10-fold higher than those observed for the single amlodipine formulations of Comparative Examples 1 and 2.

For the purpose of enhancing the stability of an amlodipine-losartan combined formulation, there has been suggested a method to optimize the pH of the composition using an acidifying or alkalifying agent. However, this method has the problem in that high pH causes hydrolysis of the ester moiety of amlodipine while low pH leads to rapid decomposition of losartan. For example, U.S. Pat. No. 6,919,087 discloses the fact that an amlodipine-losartan combined formulation whose pH is adjusted to 5.5 to 7.0 does not exhibit sufficient stability.

One of the methods for enhancing the stability of an amlodipine-losartan combined formulation is to coat the active ingredient with a coating material, but this method requires an additional coating process and the use of a fluidic layer granulating machine. In addition, in accordance with the method, it is hard to reproducibly prepare uniform combined formulation.

In accordance with one preferred embodiment, the stabilizing agent of the inventive composition is confined within the amlodipine granules. The stabilizing agent used in the present invention functions to enhance stability of amlodipine against the undesirable reaction with losartan or other pharmaceutically acceptable excipients during a blending process, and against deformation of amlodipine by light, heat or moisture with time. It is also expected that the use of the stabilizing agent leads to enhancement of stability of losartan.

The stabilizing agent used in the present invention may be preferably an anti-oxidant. Referred to as the "anti-oxidant" are materials which function to inhibit a chain reaction of automatic oxidation, decompose peroxides or inhibit an oxidation-accelerating action by metals. It is surprisingly confirmed that the use of an anti-oxidant results in significant increase of storage stability of the amlodipine-losartan combined formulation (see Table 2) for the reason that the anti-oxidant gives effects on unexpectedly inhibiting promotion of amlodipine decomposition by losartan and reducing generation of unknown impurities related to amlodipine.

Representative examples of the anti-oxidant used in the present invention include butylated hydroxytoluene (BHT), butylated hydroxyanisole (BHA), tocopherol, ascorbic acid, erythorbic acid, citric acid, ascorbyl palmitic acid, ethylene diamine tetracetic acid (EDTA), sodium pyrosulfite and a mixture thereof. Among the above anti-oxidants, neutral anti-oxidants such as butylated hydroxytoluene, butylated hydroxyanisole and tocopherol are preferred in the present invention. Acidic and basic anti-oxidants can less or more deteriorate losartan and amlodipine stabilities, respectively.

The stabilizing agent may be used in an amount ranging preferably from 0.005 to 5% by weight, more preferably from 0.01 to 1% by weight, most preferably from 0.02 to 0.5% by weight, based on the total weight of the composition.

The inventive composition may comprise pharmaceutically acceptable carriers or excipients in each of the amlodipine and losartan granules. The pharmaceutically acceptable carriers or excipients may include microcrystalline cellulose, lactose, mannitol, sodium citrate, calcium phosphate, glycine, starch, disintegrants (e.g., sodium starch glycolate, croscarmellose sodium, composite silicate and crosspovidone) and granulating binders (e.g., polyvinylpyrrolidone, hydroxypropylmethylcellulose (HPMC), hydroxypropylcellulose (HPC), sucrose, gelatine and acacia gum). Also, the inventive composition may further comprise lubricants such as magnesium stearate, stearic acid, glyceryl behenate and talc.

The inventive composition comprising the amlodipine and losartan can provide improved preventive or therapeutic effects for cardiovascular disorders such as angina pectoris, hypertension, artery vasospasm, deep vein, cardiac hypertrophy, cerebral infarct, congestive heart failure and myocardial infarction.

In accordance with one preferred embodiment, in order to make the stabilizing agent confined within the amlodipine granules, when manufacturing the amlodipine granules by way of granulating and drying a mixture of amlodipine and a pharmaceutically acceptable excipient, the stabilizing agent may be added to the mixture in the form of a powder or a solution dissolved in a solvent. Alternatively, prior to the granulation process, a mixed powder of amlodipine and the stabilizing agent may be prepared by together dissolving them in a solvent and then spray-drying the resulting solution.

In the granulation process of each of the amlodipine and losartan granules, conventional extruding-granulation, crushing-granulation, dry-granulation, fluidic layer-granulation, electromotion-granulation, electromotive fluidic layer-granulation or high-speed stirring-granulation techniques may be used. Among them, preferred are the dry-granulation, fluidic layer-granulation, and high-speed stirring-granulation techniques.

The composition of the present invention may be administered in the form of a tablet, a capsule or multi-particles through various routes of oral administration including oral cavity, mouth and hypoglossus. However, it is understood that the administration route of the inventive composition should be determined by the doctor in charge based on the patient's symptoms and requirements.

The inventive composition may be preferably formulated into the tablet form. Preferably, such a tablet obtained from the inventive composition may have an outer coating layer, and the coating layer may consist of any one of conventional high molecular compounds which are capable of forming the film coating. The amount of the coating should be reduced to a minimum for easy administration and manufacturing efficiency, and it may be in a range of about 1 to 10% by weight, preferably about 3 to 5% by weight, based on the total weight of the formulation. This coating may be performed in accordance with any one of conventional tablet coating methods. The tablet having the above composition, prepared by the above method is very stable under a conventional storage condition, and against light and moisture.

The following Examples are intended to further illustrate the present invention without limiting its scope.

EXAMPLE 1

Preparation of Combined Tablet—(I)

| - Amlodipine granule - | |
|---|---|
| amlodipine camsylate | 7.84 mg (amlodipine 5 mg) |
| butylated hydroxytoluene | 0.2 mg |
| microcrystalline cellulose | 90.0 mg |
| mannitol | 40.0 mg |
| sodium starch glycolate | 17.0 mg |
| polyvinylpyrrolidone | 5.0 mg |
| - Losartan granule - | |
| losartan potassium | 100.0 mg |
| microcrystalline cellulose | 150.0 mg |
| crosspovidone | 12.0 mg |
| - Lubricant - | |
| magnesium stearate | 4.0 mg |

Amlodipine camsylate, microcrystalline cellulose, mannitol and sodium starch glycolate were each passed through a #16 mesh and mixed in a high-speed stirrer for 3 mins, a solution containing butylated hydroxytoluene and polyvinylpyrrolidone in a mixture of purified water and ethanol was added thereto, and stirred for 5 mins. The material deposited on the inner wall of the high-speed stirrer was scrapped off and the resulting mixture was further stirred for 2 mins, dried at 60° C., and granulated to prepare amlodipine granules having specified amounts of the ingredients.

On the other hand, losartan potassium, microcrystalline cellulose and crosspovidone were mixed and dry-granulated using a roller compactor to prepare losartan granules having specified amounts of the ingredients.

The amlodipine granules were mixed with the losartan granules using a mixer for 30 minutes. Subsequently, an appropriate amount of magnesium stearate (lubricant) was added thereto, mixed for 5 mins, and the resulting mixture was formulated in the form of a combined tablet.

EXAMPLE 2

Preparation of Combined Tablet—(II)

A combined tablet was prepared by repeating the procedure of Example 1 except for using butylated hydroxytoluene in an amount of 1.0 mg.

EXAMPLE 3

Preparation of Combined Tablet—(III)

A combined tablet was prepared by repeating the procedure of Example 1 except for using 6.94 mg of amlodipine besylate (amlodipine 5 mg) instead of 7.84 mg of amlodipine camsylate.

EXAMPLE 4

Preparation of Combined Tablet—(IV)

A combined tablet was prepared by repeating the procedure of Example 3 except for using butylated hydroxytoluene in an amount of 1.0 mg.

EXAMPLE 5

Preparation of Combined Tablet—(V)

A combined tablet was prepared by repeating the procedure of Example 1 except for using 0.5 mg of butylated hydroxyanisole instead of 0.2 mg of butylated hydroxytoluene.

EXAMPLE 6

Preparation of Combined Tablet—(VI)

A combined tablet was prepared by repeating the procedure of Example 1 except for using 2.0 mg of tocopherol instead of 0.2 mg of butylated hydroxytoluene.

EXAMPLE 7

Preparation of Combined Tablet—(VII)

A combined tablet was prepared by repeating the procedure of Example 1 except for using 2.0 mg of erythorbic acid instead of 0.2 mg of butylated hydroxytoluene.

EXAMPLE 8

Preparation of Combined Tablet—(VIII)

A coated combined tablet was prepared by coating the combined tablet obtained in Example 1 with an aqueous Opadry Y-1-7000 (trade mark) solution.

COMPARATIVE EXAMPLE 1

Preparation of Amlodipine Single Tablet—(I)

| - Amlodipine granule - | |
|---|---|
| amlodipine camsylate | 7.84 mg (amlodipine 5 mg) |
| microcrystalline cellulose | 90.0 mg |
| mannitol | 40.0 mg |
| sodium starch glycolate | 17.0 mg |
| polyvinylpyrrolidone | 5.0 mg |
| - Lubricant - | |
| magnesium stearate | 3.0 mg |

Amlodipine camsylate, microcrystalline cellulose, mannitol and sodium starch glycolate were each passed through a #16 mesh and mixed in a high-speed stirrer for 3 mins, a solution containing polyvinylpyrrolidone in a mixture of purified water and ethanol was added thereto, and stirred for 5 mins. The material deposited on the inner wall of the high-speed stirrer was scrapped off and the resulting mixture was further stirred for 2 mins, dried at 60° C., and granulated to prepare amlodipine granules having specified amounts of the ingredients. Then, an appropriate amount of magnesium stearate (lubricant) was mixed with the amlodipine granules for 5 mins, and the resulting mixture was formulated in the form of a tablet.

COMPARATIVE EXAMPLE 2

Preparation of Amlodipine Single Tablet—(II)

A tablet was prepared by repeating the procedure of Comparative Example 1 except for using 6.94 mg of amlodipine besylate (amlodipine 5 mg) instead of 7.84 mg of amlodipine camsylate.

COMPARATIVE EXAMPLE 3

Preparation of Combined Tablet—(IX)

| - Amlodipine granule - | |
|---|---|
| amlodipine camsylate | 7.84 mg (amlodipine 5 mg) |
| microcrystalline cellulose | 90.0 mg |
| mannitol | 40.0 mg |
| sodium starch glycolate | 17.0 mg |
| polyvinylpyrrolidone | 5.0 mg |
| - Losartan granule - | |
| losartan potassium | 100.0 mg |
| microcrystalline cellulose | 150.0 mg |
| crosspovidone | 12.0 mg |
| - Lubricant - | |
| magnesium stearate | 4.0 mg |

A combined tablet was prepared by repeating the procedure of Example 1 except for using no butylated hydroxytoluene.

COMPARATIVE EXAMPLE 4

Preparation of Combined Tablet—(X)

A combined tablet was prepared by repeating the procedure of Comparative Example 3 except for using 6.94 mg of amlodipine besylate (amlodipine 5 mg) instead of 7.84 mg of amlodipine camsylate.

COMPARATIVE EXAMPLE 5

Preparation of Combined Tablet—(XI)

| - Granule - | |
|---|---|
| amlodipine camsylate | 7.84 mg (amlodipine 5 mg) |
| losartan potassium | 100.0 mg |
| butylated hydroxytoluene | 0.2 mg |
| microcrystalline cellulose | 90.0 mg |
| mannitol | 40.0 mg |
| sodium starch glycolate | 17.0 mg |
| polyvinylpyrrolidone | 5.0 mg |
| - Lubricant - | |
| magnesium stearate | 4.0 mg |

Amlodipine camsylate, losartan potassium, butylated hydroxytoluene, microcrystalline cellulose, mannitol and sodium starch glycolate were each passed through a #16 mesh and mixed in a high-speed stirrer for 3 mins, a solution containing polyvinylpyrrolidone in a mixture of purified water and ethanol was added thereto, and stirred for 5 mins. The material deposited on the inner wall of the high-speed stirrer was scrapped off and the resulting mixture was further stirred for 2 mins, dried at 60° C., and granulated to prepare granules having specified amounts of the ingredients. Then, an appropriate amount of magnesium stearate (lubricant) was mixed with the granules for 5 mins, and the resulting mixture was formulated in the form of a combined tablet.

Hereinafter, the compositions of formulations obtained in Examples 1 to 8 and Comparative Examples 1 to 5 are shown in Table 1.

TABLE 1

| Type | Ex. 1 | Ex. 2 | Ex. 3 | Ex. 4 | Ex. 5 | Ex. 6 | Ex. 7 | Ex. 8 | C. Ex. 1 | C. Ex. 2 | C. Ex. 3 | C. Ex. 4 | C. Ex. 5 |
|---|---|---|---|---|---|---|---|---|---|---|---|---|---|
| | Separated combined granules | | | | | | | | Single formulation | | Separated combined granules | | Not-separated combined granules |
| (a) | 7.84 | 7.84 | — | — | 7.84 | 7.84 | 7.84 | 7.84 | 7.84 | — | 7.84 | — | 7.84 |
| (b) | — | — | 6.94 | 6.94 | — | — | — | — | — | 6.94 | — | 6.94 | — |
| (c) | 90 | 90 | 90 | 90 | 90 | 90 | 90 | 90 | 90 | 90 | 90 | 90 | 90 |
| (d) | 0.2 | 1.0 | 0.2 | 1.0 | — | — | — | 0.2 | — | — | — | — | 0.2 |
| (e) | — | — | — | — | 0.5 | — | — | — | — | — | — | — | — |
| (f) | — | — | — | — | — | 2.0 | — | — | — | — | — | — | — |
| (g) | — | — | — | — | — | — | 2.0 | — | — | — | — | — | — |
| (h) | 40 | 40 | 40 | 40 | 40 | 40 | 40 | 40 | 40 | 40 | 40 | 40 | 40 |
| (i) | 17 | 17 | 17 | 17 | 17 | 17 | 17 | 17 | 17 | 17 | 17 | 17 | 17 |
| (j) | 5 | 5 | 5 | 5 | 5 | 5 | 5 | 5 | 5 | 5 | 5 | 5 | 5 |
| (k) | 100 | 100 | 100 | 100 | 100 | 100 | 100 | 100 | — | — | 100 | 100 | 100 |
| (l) | 150 | 150 | 150 | 150 | 150 | 150 | 150 | 150 | — | — | 150 | 150 | — |
| (m) | 15 | 15 | 15 | 15 | 15 | 15 | 15 | 15 | — | — | 15 | 15 | — |
| (n) | 4 | 4 | 4 | 4 | 4 | 4 | 4 | 4 | 3 | 3 | 4 | 4 | 4 |
| (o) | — | — | — | — | — | — | — | 10 | — | — | — | — | — |

(a) amlodipine camsylate
(b) amlodipine besylate
(c) microcrystalline cellulose
(d) butylated hydroxytoluene
(e) butylated hydroxyanisole
(f) tocopherol
(g) erythorbic acid
(h) mannitol
(i) sodium starch glycolate
(j) polyvinylpyrrolidone
(k) losartan potassium
(l) microcrystalline cellulose
(m) crosspovidone
(n) magnesium stearate
(o) Opadry Y-1-7000

TEST EXAMPLE 1

Stability Test Against Light

A light-stability test was performed for the tablets obtained in Examples 1 to 8 and Comparative Examples 1 to 5 by measuring amounts of impurities generated under the following conditions. The results are shown in Table 2.

—Chamber Condition—
Apparatus: Xe-3-HC available from Q-Lab Company
Temperature and humidity: 25° C.±2° C./60%±5% RH
Illumination: 0.80 W/m²/nm (1,200,000 lux-ICH guideline), 18.44 hrs
Sample storage: petridish
—Test Point—
Before test and after 1,200,000 lux light exposure
—Analytical Condition (Impurities Related to Amlodipine)—
Column: stainless steel column (inner diameter: 4.6 mm, length: 15 cm) filled with octadecylsilanized silica gel for 5 μm liquid chromatography
Mobile phase: phosphate buffer:acetonitrile (58:42, v/v)
Detector: ultraviolet spectrophotometer (237 nm)
Flow rate: 1.2 ml/min
Temperature: 40° C.
Injection volume: 10 μl
Extraction solution: mobile phase
—Analytical Condition (Impurities Related to Losartan)—
Column: stainless steel column (inner diameter: 4.6 mm, length: 15 cm) filled with octadecylsilanized silica gel for 5 μm liquid chromatography
Mobile phase A: phosphate buffer:acetonitrile (850:150, v/v)
Mobile phase B: acetonitrile
Concentration gradient system

| Time (min) | Mobile phase A % | Mobile phase B % |
|---|---|---|
| 0 | 80 | 20 |
| 10 | 40 | 60 |
| 11 | 80 | 20 |
| 15 | 80 | 20 |

Detector: ultraviolet spectrophotometer (250 nm)
Flow rate: 1.5 ml/min
Injection volume: 10 μl
Extraction solution: mobile phase

TEST EXAMPLE 2

Accelerated Stability Test

An accelerated stability test was performed for the tablets obtained in Examples 1 to 8 and Comparative Examples 1 to 5 by measuring amounts of impurities generated under the following conditions. The results are shown in Table 2.

—Chamber Condition—
Temperature: 50° C.±2° C.
Sample storage: HDPE bottle
—Test Point—
Before test and after stored for 28 days —Analytical Condition—
Identical to that of Test Example 1

TABLE 2

|  | Before test (% by weight) | | | After light exposure (Test Ex. 1) (% by weight) | | | After stored for 28 days (Test Ex. 2) (% by weight) | | |
| --- | --- | --- | --- | --- | --- | --- | --- | --- | --- |
|  | (a) | (b) | (c) | (a) | (b) | (c) | (a) | (b) | (c) |
| Ex. 1 | N.D. | 0.02 | 0.04 | 0.11 | 0.20 | 0.08 | 0.03 | 0.12 | 0.10 |
| Ex. 2 | N.D. | 0.01 | 0.05 | 0.07 | 0.15 | 0.06 | 0.02 | 0.08 | 0.09 |
| Ex. 3 | 0.01 | 0.03 | 0.04 | 0.33 | 0.40 | 0.07 | 0.10 | 0.14 | 0.12 |
| Ex. 4 | N.D. | 0.04 | 0.05 | 0.28 | 0.30 | 0.07 | 0.08 | 0.10 | 0.15 |
| Ex. 5 | N.D. | 0.03 | 0.06 | 0.10 | 0.15 | 0.08 | 0.04 | 0.07 | 0.09 |
| Ex. 6 | N.D. | 0.03 | 0.05 | 0.17 | 0.23 | 0.05 | 0.07 | 0.11 | 0.11 |
| Ex. 7 | N.D. | 0.02 | 0.05 | 0.14 | 0.19 | 0.19 | 0.04 | 0.08 | 0.52 |
| Ex. 8 | N.D. | 0.04 | 0.07 | 0.02 | 0.09 | 0.08 | 0.03 | 0.10 | 0.18 |
| C. Ex. 1 | N.D. | 0.02 | — | 0.21 | 0.38 | — | N.D. | 0.03 | — |
| C. Ex. 2 | N.D. | 0.02 | — | 1.28 | 1.45 | — | N.D. | 0.09 | — |
| C. Ex. 3 | N.D. | 0.04 | 0.06 | 0.86 | 1.01 | 0.16 | 0.15 | 0.68 | 0.22 |
| C. Ex. 4 | N.D. | 0.03 | 0.05 | 3.89 | 4.13 | 0.17 | 0.57 | 0.65 | 0.39 |
| C. Ex. 5 | 0.04 | 0.18 | 0.20 | 1.09 | 1.17 | 0.31 | 0.59 | 1.27 | 0.82 |

(a) amlo-pyridine
(b) impurities related to amlodipine
(c) impurities related to losartan As can be seen from Table 2, the combined tablets prepared by using the stabilizing agent as well as the separated granules of amlodipine and losartan according to Examples 1 to 8 generated even smaller amounts of amlo-pyridine, and impurities related to amlodipine and losartan under the light exposure or severe storage condition, thereby exhibiting higher storage stability, as compared with the combined tablets obtained in Comparative Examples 3 to 5. In addition, some combined tablets prepared in Examples generated smaller amounts of impurities, thereby exhibiting higher storage stability, even as compared with the single amlodipine formulations obtained in Comparative Examples 1 and 2.

Especially, it is confirmed that the tablets prepared in Comparative Examples 3 to 5 did not satisfy the stability criteria required in the ICH guideline, i.e., generation of 0.5% by weight or less of impurities related to amlodipine under a storage condition even though the structures of the impurities were well known.

While the invention has been described with respect to the above specific embodiments, it should be recognized that various modifications and changes may be made to the invention by those skilled in the art which also fall within the scope of the invention as defined by the appended claims.

What is claimed is:

1. A solid pharmaceutical composition comprising granular forms of amlodipine and losartan which are separated from each other, and a stabilizing agent,
    wherein the stabilizing agent is an antioxidant selected from the group consisting of butylated hydroxytoluene, butylated hydroxyanisole, tocopherol, ascorbic acid, erythorbic acid, citric acid, ascorbyl palmitic acid, ethylene diamine tetracetic acid, sodium pyrosulfite, and a mixture thereof; and
    wherein the stabilizing agent is used in an amount ranging from 0.005 to 5% by weight based on the total weight of the composition.

2. The composition of claim 1, wherein the anti-oxidant is a neutral anti-oxidant.

3. The composition of claim 2, wherein the neutral antioxidant is butylated hydroxytoluene, butylated hydroxyanisole, or tocopherol.

4. The composition of claim 1, wherein the stabilizing agent is confined within the amlodipine granules.

5. The composition of claim 1, wherein the stabilizing agent is used in an amount ranging from 0.01 to 1% by weight based on the total weight of the composition.

6. The composition of claim 5, wherein the stabilizing agent is used in an amount ranging from 0.02 to 0.5% by weight based on the total weight of the composition.

7. The composition of claim 1, wherein amlodipine and losartan are used in a weight ratio of the range of 1:1 to 1:40.

8. A method of treating a cardiovascular disorder comprising administering the composition of claim 1 in an effective amount into a subject in need thereof.

9. The method of claim 8, wherein the cardiovascular disorder is selected from the group consisting of angina pectoris, hypertension, artery vasospasm, deep vein, cardiac hypertrophy, cerebral infarct, congestive heart failure, and myocardial infarction.

* * * * *